United States Patent [19]
Zaromb

[11] Patent Number: 6,087,183
[45] Date of Patent: Jul. 11, 2000

[54] HIGH-THROUGHPUT LIQUID-ABSORPTION AIR-SAMPLING APPARATUS AND METHODS

[76] Inventor: Solomon Zaromb, 95706 William Dr., Hinsdale, Ill. 60521

[21] Appl. No.: 08/851,428

[22] Filed: May 5, 1997

Related U.S. Application Data

[63] Continuation-in-part of application No. 08/255,712, Jun. 7, 1994, abandoned, and a continuation-in-part of application No. 08/377,966, Jan. 25, 1995, Pat. No. 8,255,712, which is a continuation-in-part of application No. 07/931,572, Aug. 10, 1992, abandoned, and a continuation of application No. 07/993,080, Dec. 18, 1992, Pat. No. 5,328,851, which is a division of application No. 07/499,602, Mar. 26, 1990, Pat. No. 5,173,264, which is a continuation-in-part of application No. 07/330,654, Mar. 30, 1989, Pat. No. 4,942,135, and a continuation-in-part of application No. 07/330,655, Mar. 30, 1989, Pat. No. 4,977,095, said application No. 08/255,712, is a continuation-in-part of application No. 07/931,572.

[51] Int. Cl.[7] ................................................... G01N 1/18
[52] U.S. Cl. ........................... 436/178; 436/52; 422/88; 422/68.1; 422/52; 422/91; 55/423
[58] Field of Search ........................ 422/52, 56, 88, 422/91, 89, 98, 68.1; 436/51–55, 165, 167, 178, 168, 172, 609, 161, 169; 55/423, 428

[56] References Cited

U.S. PATENT DOCUMENTS 5,173,264  12/1992  Zaromb et al. ........................ 422/88

*Primary Examiner*—Lyle A. Alexander

[57] ABSTRACT

A portable high-throughput liquid-absorption air sampler [PHTLAAS] has an asymmetric air inlet through which air is drawn upward by a small and light-weight centrifugal fan driven by a direct current motor that can be powered by a battery. The air inlet is so configured as to impart both rotational and downward components of motion to the sampled air near said inlet. The PHTLAAS comprises a glass tube of relatively small size through which air passes at a high rate in a swirling, highly turbulent motion, which facilitates rapid transfer of vapors and particulates to a liquid film covering the inner walls of the tube. The pressure drop through the glass tube is <10 cm of water, usually <5 cm of water. The sampler's collection efficiency is usually >20% for vapors or airborne particulates in the 2–3$\mu$ range and >50% for particles larger than 4$\mu$. In conjunction with various analyzers, the PHTLAAS can serve to monitor a variety of hazardous or illicit airborne substances, such as lead-containing particulates, tritiated water vapor, biological aerosols, or traces of concealed drugs or explosives.

46 Claims, 11 Drawing Sheets

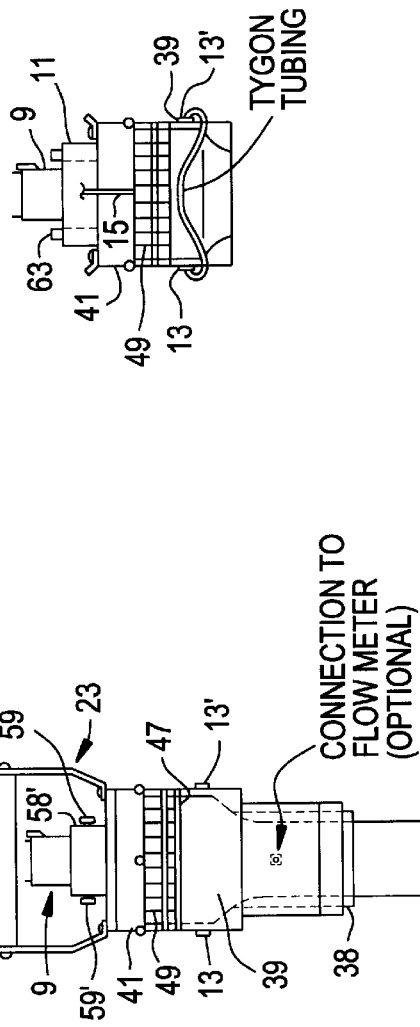
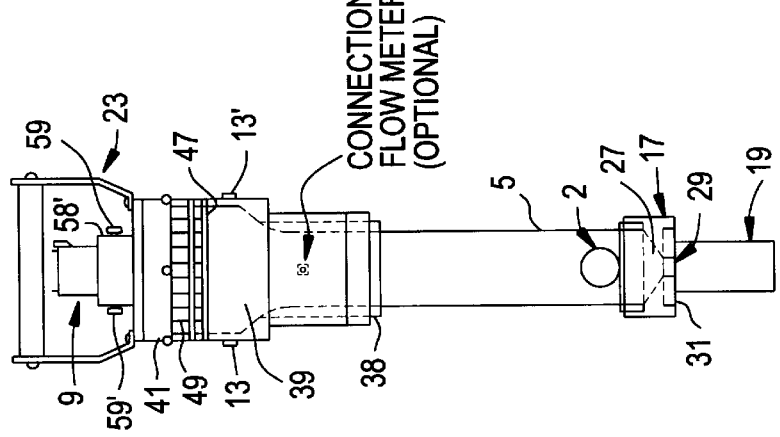
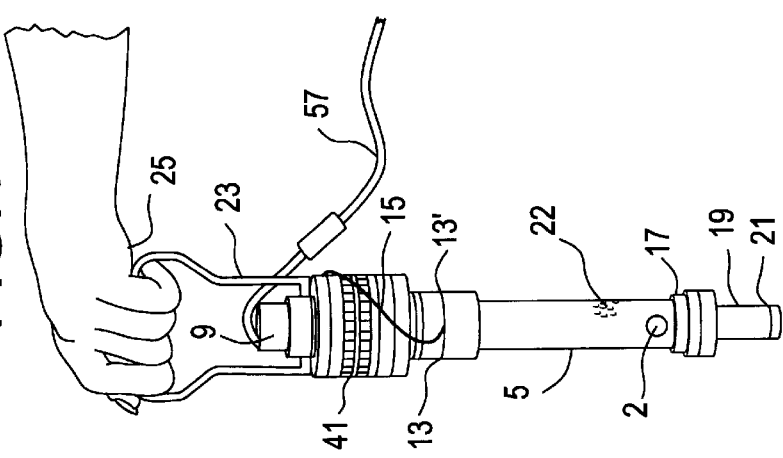

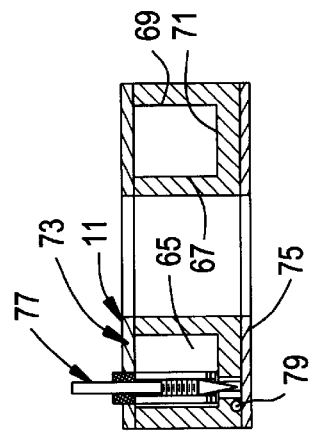
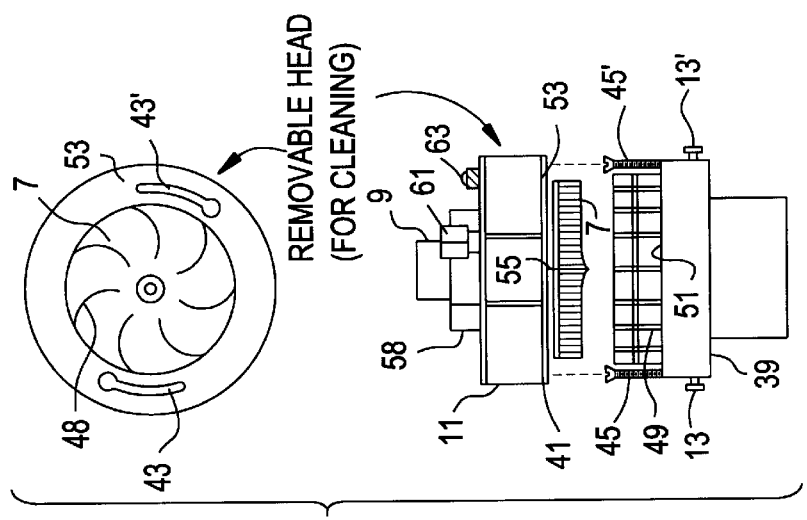
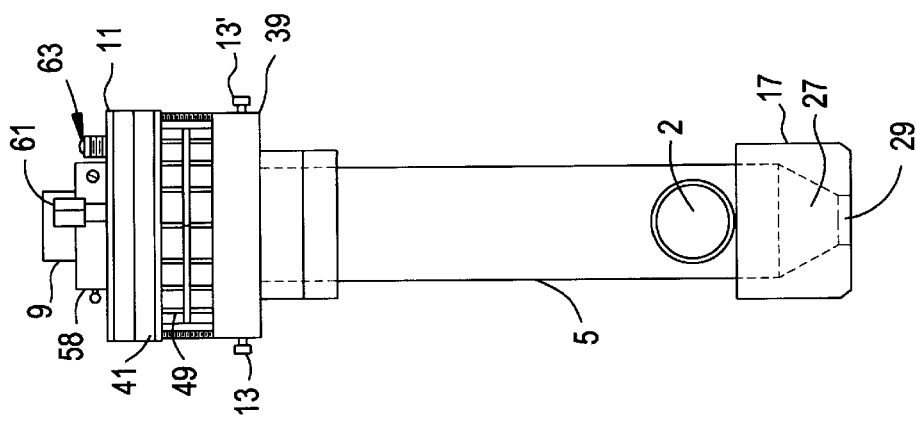

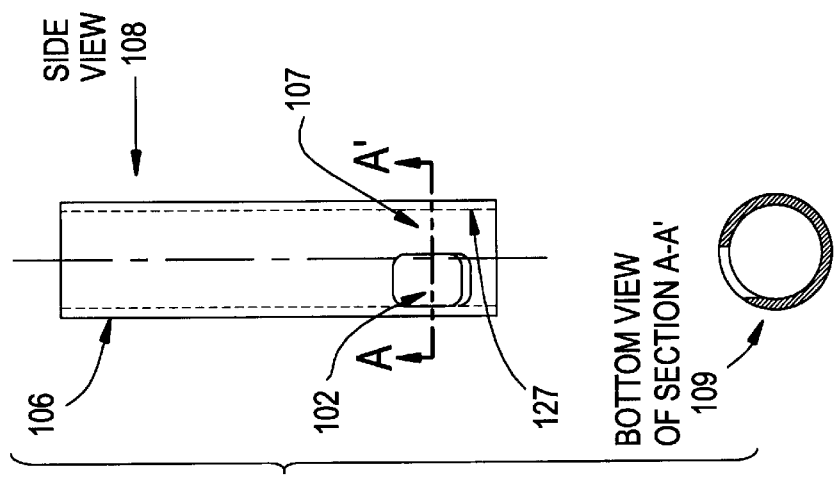
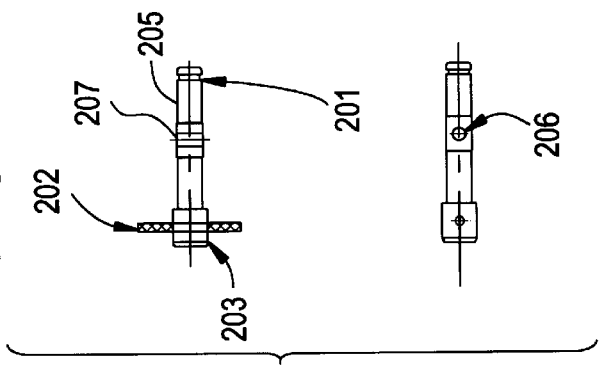
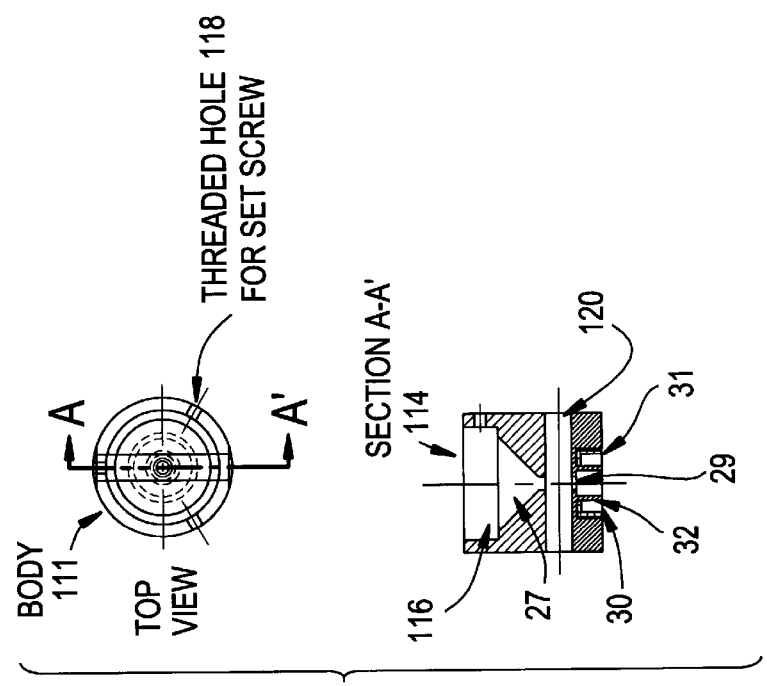

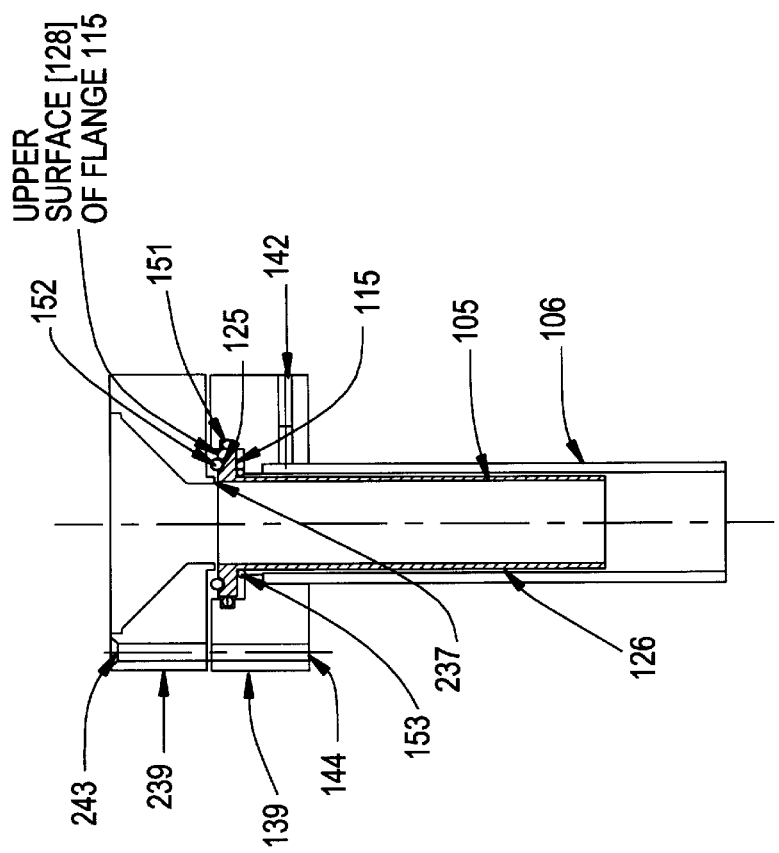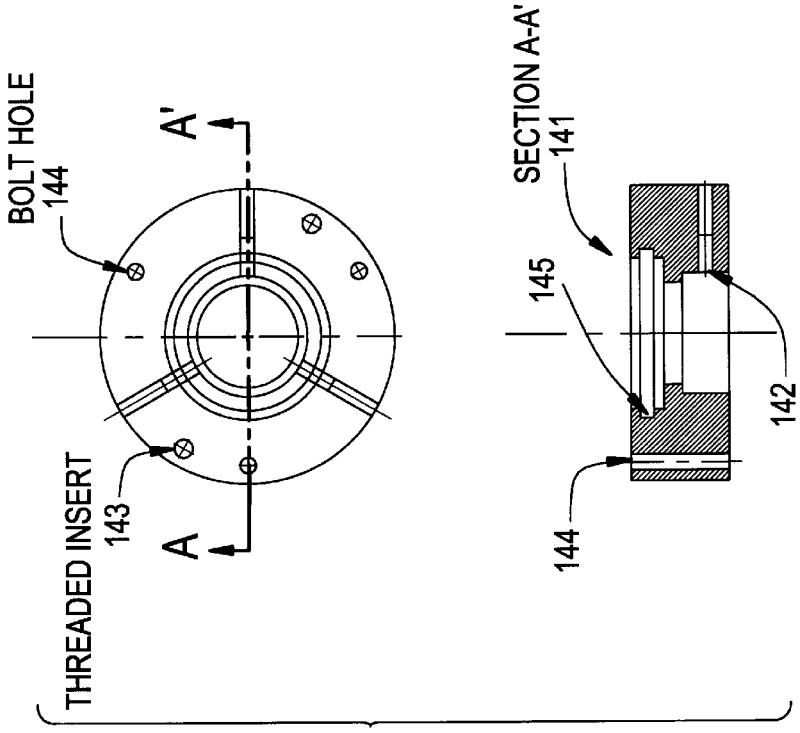

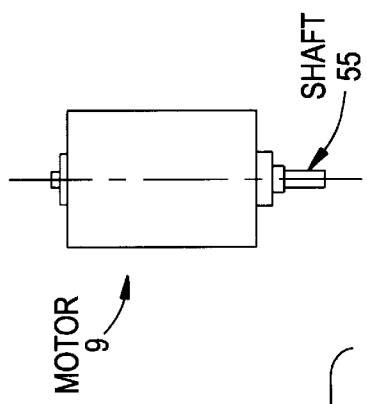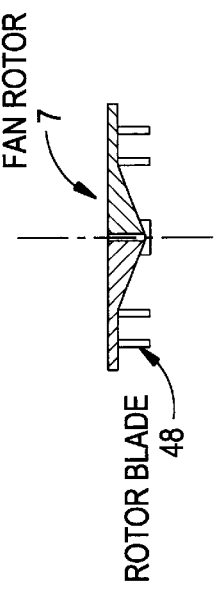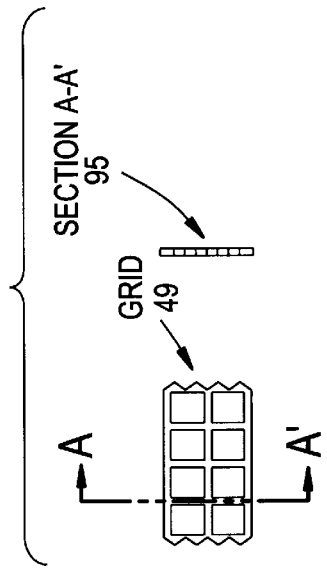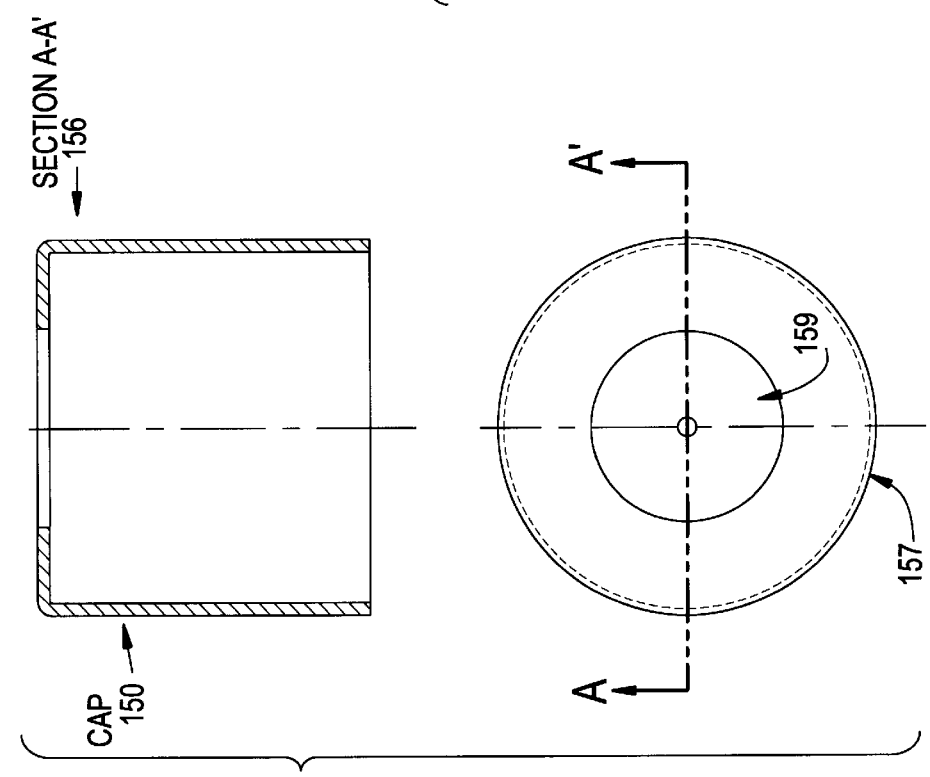

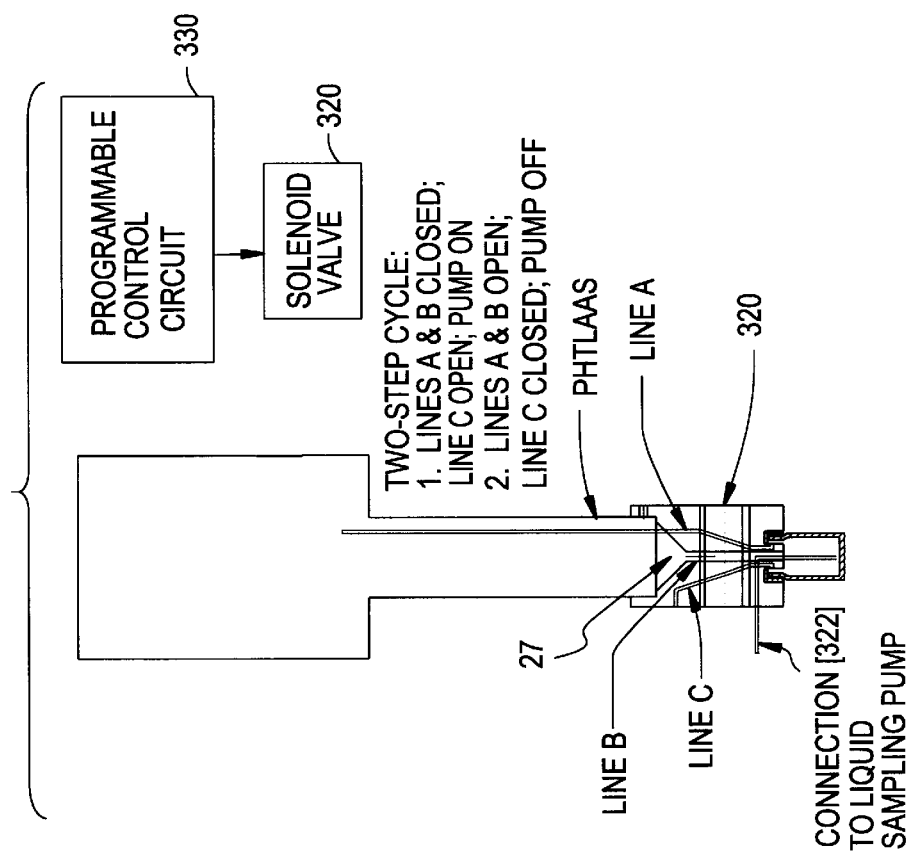
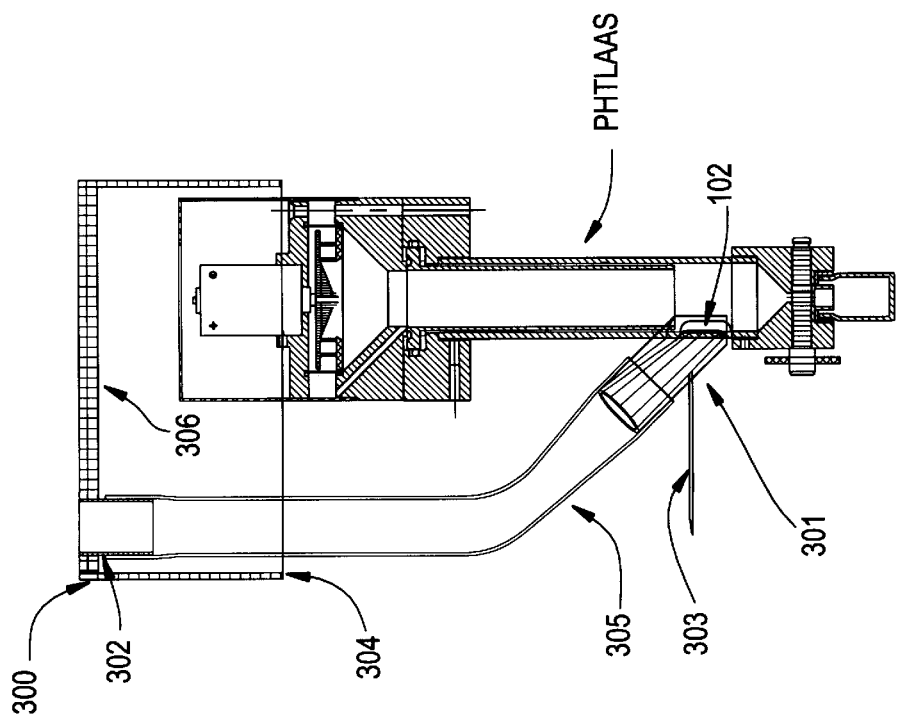

HIGH-THROUGHPUT LIQUID-ABSORPTION AIR-SAMPLING APPARATUS AND METHODS

REFERENCE TO RELATED APPLICATIONS

This is a continuation-in-part of application Ser. No. 08/255,712, filed Jun. 7, 1994, now abandoned, and a CIP of Ser. No. 08/377,966, filed Jan. 25, 1995. Application Ser. No. 08/255,712 is a continuation-in-part of application Ser. No. 07/931,572, filed Aug. 10, 1992, now abandoned. Application Ser. No. 08/377,966 is a CIP of Ser. No. 07/931,572 and a continuation of application Ser. No. 07/993,080, filed Dec. 18, 1992, now U.S. Pat. No. 5,328,851 which was a divisional application of application Ser. No. 07/499,602, filed Mar. 26, 1990, now U.S. Pat. No. 5,173,264, which was a continuation-in-part of U.S. application Ser. No. 07/330,654, filed Mar. 30, 1989, now U.S. Pat. No. 4,942,135, and Ser. No. 07/330,655, filed Mar. 30, 1989, now U.S. Pat. No. 4,977,095, the disclosures of all of which are incorporated herein by reference.

CONTRACTUAL ORIGIN OF THE INVENTION

The United States Government has rights in this invention pursuant to Contract No. W-31-109-ENG-38 between the U.S. Department of Energy and The University of Chicago representing Argonne National Laboratory.

BACKGROUND OF THE INVENTION

The present invention relates to analytical instruments for detecting and identifying low concentrations of selected air-borne vapors or particulates, and especially to portable instruments. The present invention has particular application to rapid detection and identification of trace air contaminants such as vapors of cocaine, heroin, explosives, radioactive substances, and other substances that may be carcinogenic, highly toxic, or of forensic interest. More specifically, the invention relates to portable high-throughput liquid-absorption air-sampling apparatus and methods.

Liquid-absorption sampling has been used successfully for the collection of many different analyte vapors, including those of trinitrotoluene, alkaloids, primary aromatic amines, hydrazines, hydrogen peroxide, nitrogen oxide, diisocyanates, 2-chloronitrobenzene, and several inorganic halogen compounds (HCl, HF, $F_2$, and other hydrolyzable fluorides). Preferably, as disclosed in my U.S. Pat. No. 5,328,851, the extractant should react rapidly with the analyte to yield a product that can be measured electrochemically, preferably using a miniaturized amperometric or potentiometric sensor, or photometrically, e.g., colorimetrically or by chemiluminescence, using a built-in, preferably fiber-optic, detector. This should yield a portable yet highly sensitive, near real-time, self-contained analytical instrument. Alternatively, near real-time recording of sampled air compositions can be obtained by feeding the collected liquid into separate properly marked vials at pre-determined intervals.

It is also recognized that many chemical compounds tend to be preferentially adsorbed onto solid surfaces, especially air-borne solid particulates, or absorbed by liquids, especially water droplets. This is true of most explosives and at least some propellants and chemical warfare agents. Therefore, suspended liquid and solid particulates may serve as natural pre-concentrators. It may be advantageous to collect analytes from air-borne water droplets and/or particulates. This advantage is not readily offered by alternative types of pre-concentrators.

U.S. Pat. No. 5,328,851 discloses an advanced high-throughput liquid-absorption pre-concentrator (HTLAP) which incorporates the pre-concentrating sampler of U.S. Pat. No. 4,977,095 and the analytical system of U.S. Pat. No. 4,942,135, and which further provides for rapid detection and analysis of air-borne contaminants that may be in form of vapor or contained in aerosols.

Also, as a continuation-in-part of co-pending application Ser. No. 08/377,966, this invention relates to apparatus and methods for monitoring the concentrations of hazardous substances contained in respirable particulates, especially lead in fire ranges, in and around lead-smelting or lead-fabricating facilities, lead-acid battery or pottery and ceramic plants, radiator repair and other soldering shops, dwellings contaminated with chipping lead paint, and other locations were elevated respirable levels may pose a hazard to human health.

It is therefore the purpose of this invention to provide a cost-effective method and instrumentation for monitoring airborne lead concentrations in said locations to help prevent lead poisoning among exposed persons.

In copending application Ser. No. 08/377,966, reference is made to a portable HTLAP device as one of two alternative means for collecting lead-containing particulates and solubilizing them in a liquid extractant. The present invention is addressed specifically to the realization of a portable HTLAP. The HTLAP that is disclosed in my U.S. Pat. No. 5,328,851 is a "transportable unit" which can not be easily carried single-handedly.

It is therefore another object of this invention to provide an inexpensive, portable, and rapid means for estimating airborne concentrations of lead or of other hazardous air contaminants using a portable high-throughput liquid-absorption air sampler [PHTLAAS].

The "transportable" HTLAP that is disclosed in U.S. Pat. No. 5,328,851 uses an elongated vertical tube with a wetted interior wall along whose surface a liquid film is caused to drain down by gravity. The vertical drainage is incompatible with efficient operation of the sampler at different orientations, especially those approaching the horizontal one. However, during inspections for illicit drugs or explosives, it may be necessary to insert the PHTLAAS into nooks, crannies or horizontal slots between closely stacked crates in order to pick up traces of hidden illicit substances.

It is therefore another object of the invention to provide methods of using the PHTLAAS as a probe that can be operated in any arbitrary orientation while still retaining a capability for picking up low concentrations of vapors or air-borne particulates.

The HTLAP that is disclosed in U.S. Pat. No. 5,328,851 requires that the sampled air not be exposed to unheated dry surfaces before coming in contact with a liquid absorbing film that is draining down its wetted interior wall. This requirement would make it difficult or impossible to operate the sampler at orientations that are highly inclined from the vertical direction.

It is therefore another object of this invention to provide methods of efficiently operating HTLAP and especially PHTLAAS devices without their interior wall being mostly wetted.

Previously reported high-throughput liquid-absorption air scrubbers, including the HTLAP that is disclosed in my U.S. Pat. No. 5,328,851, require an air suction of >30 cm of water, possibly even >100 cm of water, and consequently a heavy pump and a rather large power input for their operation. They also utilize a liquid-supply reservoir and a liquid-metering pump. These features are incompatible with compact and light-weight devices that can be conveniently hand-carried.

It is therefore still another object of this invention to provide a PHTLAAS that can operate without a liquid-metering pump, without a liquid reservoir or with a substantially inconspicuous reservoir, and at a relatively low suction that can be effected by a small and light-weight D.C.-powered fan.

The HTLAP that is disclosed in my U.S. Pat. No. 5,328,851 uses an aqueous liquid extractant that is not readily compatible with certain analytical instruments, such as a gas chromatograph [GC] or an ion mobility spectrometer [IMS].

It is therefore still another object of this invention to render the HTLAP, and especially the PHTLAAS, conveniently usable with GC, IMS, and other instruments that are not geared for analyzing aqueous samples.

Radio-active substances, such as tritium or tritiated water, are encountered in nuclear reactor facilities. It may be important to monitor the concentrations of such substances in air over short time intervals. It is therefore yet another object of this invention to provide methods of monitoring the concentrations of radioactive substances in air, especially of tritiated water, with the aid of a PHTLAAS.

Other objects of the invention will become apparent to professionals in the health monitoring, industrial safety and hygiene, environmental, metallurgical, forensic, and related areas following perusal of the complete specification.

SUMMARY OF THE INVENTION

Briefly, the invention consists of providing a portable high-throughput liquid-absorption air sampler [PHTLAAS] through which air is drawn upward at a fast rate by a small and light-weight centrifugal fan driven by a DC [direct current] motor that can be powered by a battery. An asymmetric air inlet combined with the rotation of the fan impart a partly downward and rotational motion to the in-rushing air. The PHTLAAS comprises a glass tube of relatively small size, e.g., about 2.7 cm I.D., through which air passes at a high rate, e.g., 200–300 L/min, in a swirling, highly turbulent motion, which facilitates rapid transfer of particulates and trace vapor constituents to a liquid film covering the inner walls of the tube. The pressure drop through the glass tube is <10 cm of water, usually <5 cm of water, as compared with 100–260 cm in earlier large-air-volume liquid scrubbers or with about 30 cm of water in the "transportable" unit that is disclosed in my U.S. Pat. No. 5,328,851. The partial flow reversal within the sampler from partly downward near the air inlet to an upward direction in the glass tube increases the tendency of particulates to impinge upon the walls of the sampler and be captured by the liquid film, thereby improving the sampler's collection efficiency.

The PHTLAAS collects from the sampled air a substantial fraction, usually >20%, of airborne vapors and particulates. After rapidly solubilizing the hazardous substance of interest (analyte), such as lead, from the collected particulates into a sample of liquid extractant, the extractant sample contains a sufficiently high concentration of analyte that can be determined with the aid of an appropriate analyzer. For instance, rapid solubilization of lead is achieved by a liquid extractant comprising 0.1–1 M of acetic acid or acetate, preferably at a pH of 5 or less and preferably with inclusion of 1–10% of hydrogen peroxide. Rapid determination of the lead content in the liquid extractant may be effected with an indicator tape or an electrochemical analyzer.

The PHTLAAS does not require any liquid pump and can be operated without a liquid reservoir or with a small reservoir. To operate the PHTLAAS without a reservoir it suffices to inject a relatively small volume of liquid, such as 5–20 mL, into the air inlet opening prior to the sampling step. To supply the liquid continuously during a sampling operation, a small reservoir, having a capacity of preferably 40–50 mL, may be provided, preferably above the fan portion of the PHTLAAS, and the suction of the fan may be sufficient to draw liquid from the reservoir into the wetted sampling tube at a fixed rate that may be controlled by a needle valve.

Operation of the PHTLAAS at a nearly horizontal orientation is facilitated by a funnel portion between the wetted air-sampling tube and the fan and by rinsing the tube in a nearly vertical orientation following the sampling step. Rapid and effective rinsing and cleaning of the sampler is facilitated by a provision for easy removal and reconnection of the fan portion of the PHTLAAS from the funnel portion.

The PHTLAAS offers advantages for rapid and/or ultrasensitive detection and analysis of trace air contaminants resulting from (a) its high air-sampling rate, (b) an appreciable analyte collection efficiency for both vapors and aerosols, and (c) the low volume of collected liquid absorbent. These three features combine to reduce the lower detection limit of available analytical instrumentation by a factor of >100 and/or to permit faster sampling and far more rapid on-site air monitoring than were previously practicable. Other attractive features of the PHTLAAS include applicability to most analytes and compatibility with most analytical devices, particularly those geared for the detection of analytes in liquid, especially aqueous, samples.

This technology may also be useful to help meet the requirements of industry and regulatory agencies to monitor work environments and waste stream effluents for powerful carcinogens, such as dioxins or radionucleides, and for other highly hazardous substances. By coupling a PHTLAAS with existing analyzers the detection sensitivities for such substances can be increased by several orders of magnitude.

Additional objects, advantages and novel features of the invention will be set forth in part in the description which follows, and in part will become apparent to those skilled in the art upon examination of the following drawings or may be learned by practicing the invention. The objects and advantages of the invention may be realized and attained by means of the instrumentalities and combinations particularly pointed out in the appended claims.

BRIEF DESCRIPTION OF THE DRAWINGS

For the purpose of facilitating an understanding of the invention there are illustrated in the accompanying drawings preferred embodiments thereof, from an inspection of which, when considered in connection with the following description, the invention, its construction and operation, and many of its advantages should be readily understood and appreciated.

FIG. 1 is an outline of a photograph of an early version of a PHTLAAS in accordance with the present invention;

FIG. 2A is a schematic drawing of a slightly modified version of the PHTLAAS of FIG. 1;

FIG. 2B is a schematic drawing of the upper portion of the PHTLAAS of FIG. 3A;

FIGS. 2C and 2D are two views of a schematic drawing of a beveled air inlet hole and a Teflon plug with a matching bevel fitting snugly into the inlet hole;

FIG. 3A is a partial schematic drawing of a slightly different version of the PHTLAAS of FIG. 1;

FIG. 3B is a schematic drawing showing the bottom and side views of an easily removable fan portion of the PHTLAAS of FIG. 3A and a side view of a funnel portion into which the fan portion can be readily locked;

FIG. 4 is a cross sectional view of the liquid reservoir 11 of FIGS. 2B, 3A, and 3B;

FIG. 6 is a top view and a corresponding axial cross-sectional view of the body 111 of drain portion 117 of the PHTLAAS of FIG. 5;

FIG. 7 shows two orthogonal side views of the drain valve 100 of FIG. 5;

FIG. 8 is a side view and a corresponding bottom view of section A—A' of the outer tube 105 of FIG. 5;

FIG. 10 is a top view and a corresponding axial cross-sectional view of the coupling ring 139 of FIG. 5;

FIG. 12 is a schematic, incompletely hatched, axial sectional view showing how the coupling of ring 139 to funnel 239 results in a firm, well-cushioned seating by three O-rings of the inner glass tube 105 of FIG. 5;

FIG. 16A is a top view and a corresponding axial cross-sectional view of the cap 150 of FIG. 5;

FIG. 16B is a side view of the motor 9 of FIG. 5;

FIG. 16C shows a side view and a cross-sectional view of the spacing grid 49 of FIG. 5;

FIG. 16D is an axial cross-sectional view of the fan rotor 7 of FIG. 5;

FIG. 17 is a schematic cross-sectional view of a sampler that is provided with an air intake adapter for sampling air from the outside of an enclosure;

FIG. 18 is a schematic block diagram of an interface between a PHTLAAS and one or more sensors.

DESCRIPTION OF THE PREFERRED EMBODIMENTS

Figure 5:
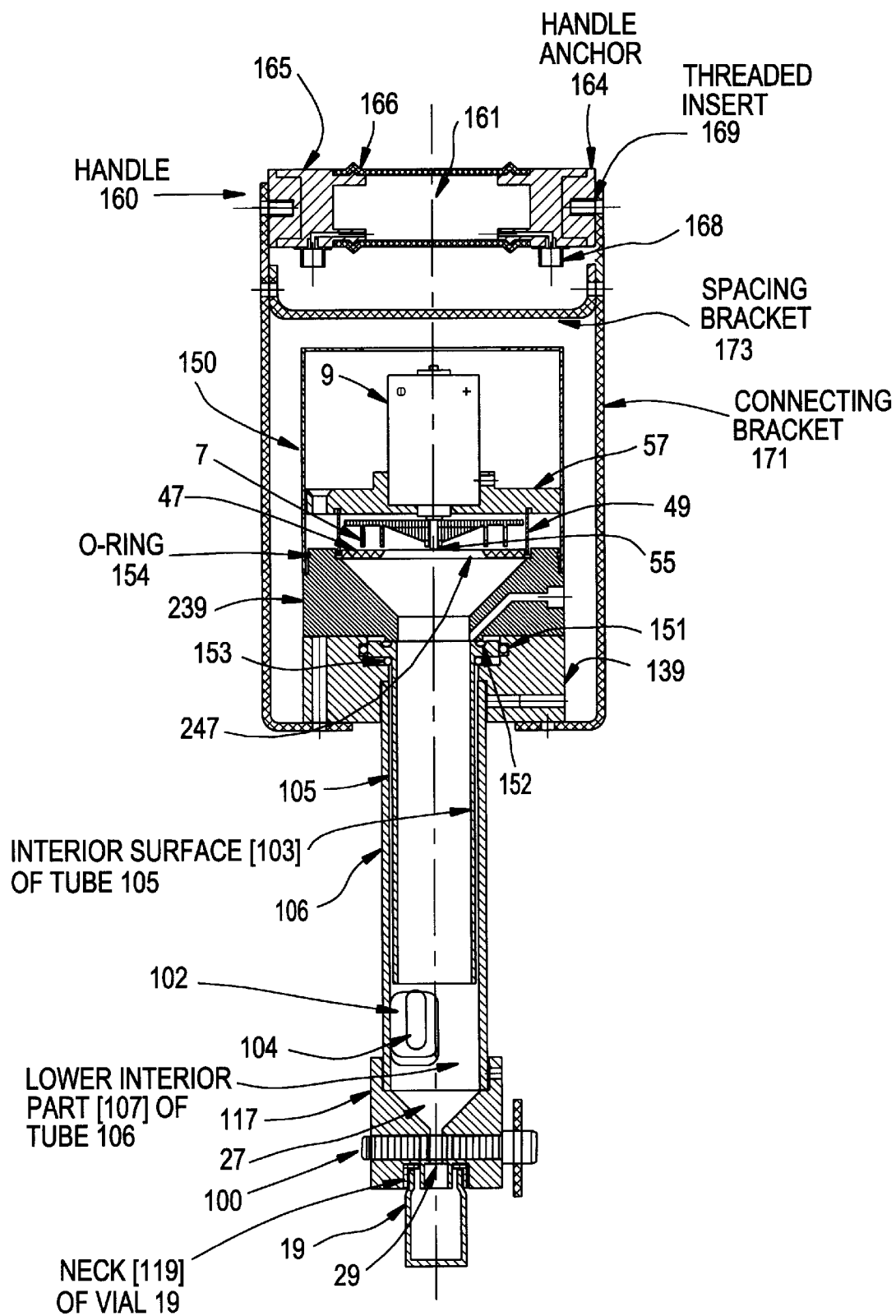
FIG. 5 is a cross-sectional view of a preferred embodiment of a ruggedized field-usable PHTLAAS.

Referring to FIG. 1, there is shown an outline of a photograph of an early version of a PHTLAAS made in accordance with the principles of the present invention.

In operation, the air that is to be sampled, which contains traces of the analyte of interest, is drawn in through an inlet 2 into a sampling tube 5 by a centrifugal fan assembly 41 that includes a driving motor 9. The analyte-sorbing liquid, which is selected to preferentially absorb the analyte of interest, is supplied from a reservoir 11 [FIG. 2B] into two liquid inlet holes 13, 13' by a tubule 15 that is connected to a flow-controlling needle valve 77 via a channel 79 [FIG. 4].

The liquid drains down the interior wall of tube 5, so as to absorb traces of the analyte of interest from the sampled air flowing through tube 5, and drips through a funnel-shaped drain portion 17 into a collecting vial 19.

Figure 11:
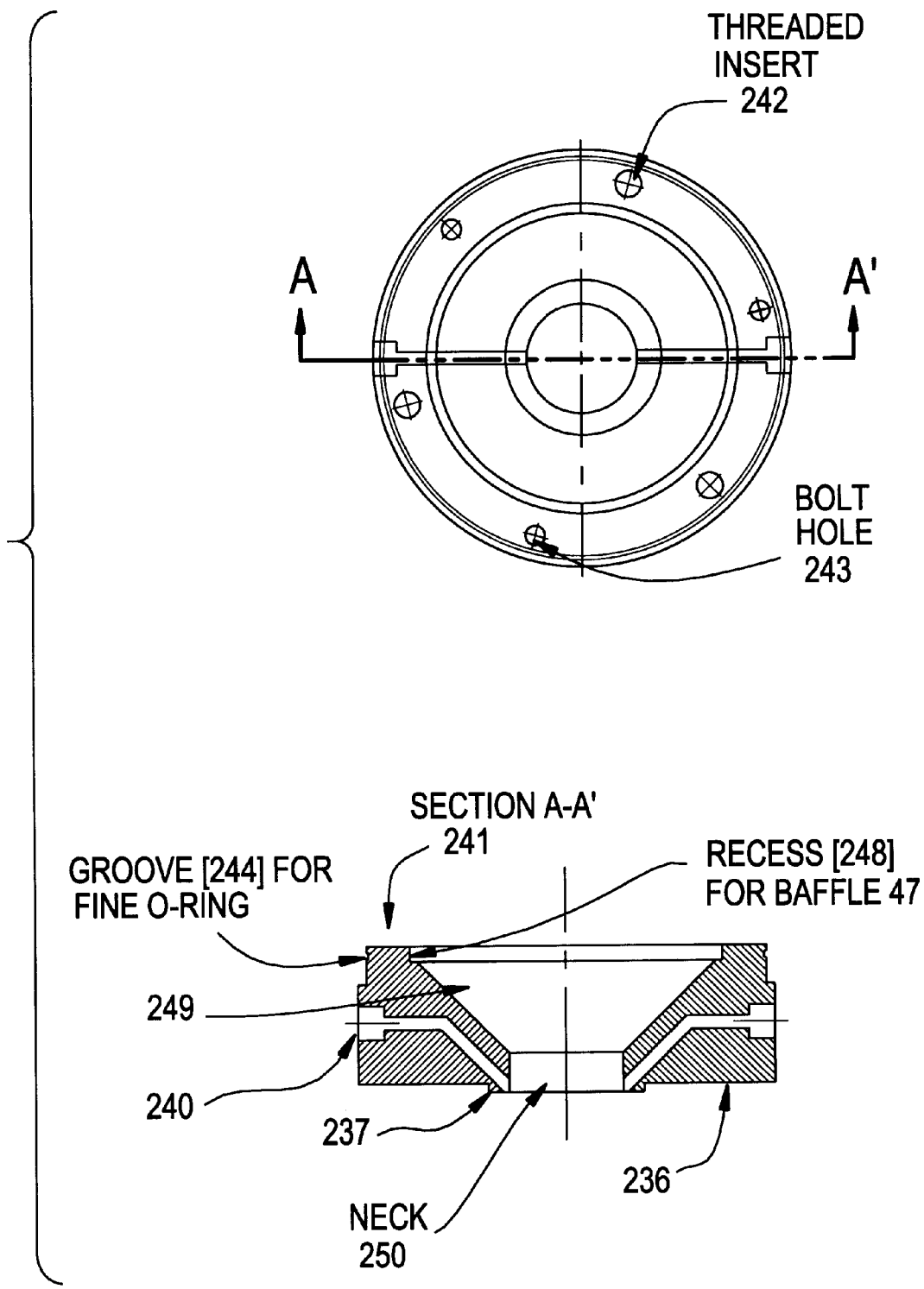
FIG. 11 is a top view and a corresponding axial cross-sectional view of the upper funnel portion 239 of FIG. 5.
Figure 15:
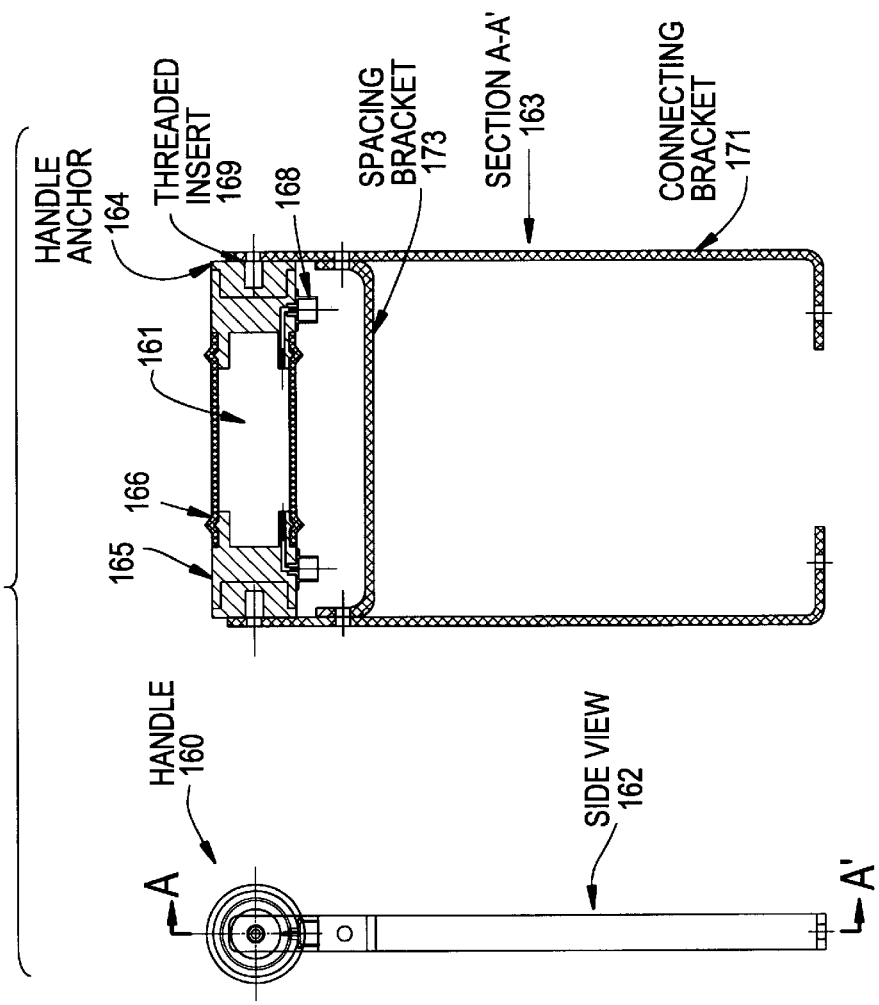
FIG. 15 shows a side view and a corresponding cross-sectional view of the handle 160 and spray reservoir 161 of FIG. 5.

Also seen in FIG. 1 are an analyte-enriched liquid 21 collected in vial 19, swirls 22 in the liquid film covering the inner walls of tube 5, and a handle 23 for carrying the PHTLAAS by a hand 25. The uppermost part of handle 23 may comprise a liquid reservoir 161 [FIGS. 5 and 15] enclosed by a piece of Tygon tubing 166 and two rotatable couplings 165. Each coupling 165 comprises a fine channel leading from reservoir 161 to a Luer fitting 168, from which a tubule can be connected to one of the liquid inlets 13, 13' [FIGS. 1–3] or 240 [FIG. 11].

The design and operation of the PHTLAAS of FIG. 1 are best explained with reference to FIGS. 2–4. In FIGS. 2A and 3A are outlined most of the main components of the PHTLAAS of FIG. 1, including the air inlet 2, the sampling tube 5, the fan assembly 41 with motor 9, the liquid inlet openings 13, 13', and the drain portion 17. As indicated in FIG. 2A, drain portion 17 comprises a conical cavity 27 terminating at a drain port 29, which is a hole drilled along the axis of drain portion 17 all the way through a vial cap 31 that is affixed to the bottom of drain 17. Port 29 can be plugged with a stopper [not shown], so as to permit partial recirculation and evaporation of the analyte-enriched liquid, or it may be left unplugged when continuous draining of the liquid is desired. Vial 19, used to collect the drippings through port 29, has threads at the outside of its upper neck 119 that screw into matching threads in cap 31 [see FIG. 5]. The matching threads permit quick attachment and removal of vial 19 by a simple screwing and unscrewing motion.

As shown in FIG. 2C, the lower end of sampling tube 5 has a collar 33 that fits snugly into the upper part of drain portion 17. Right above collar 33 is the air inlet 2, which is a bevelled hole 34 into which can be fitted the conically shaped plug 35 of FIG. 2D. Plug 35, preferably made of polytetrafluoroethylene or polypropylene, is a ¼" thick slice of a 45° cone whose upper base is 1" in diameter and lower base is ½" in diameter. A ½" diameter hole 37 drilled through plug 35 at an angle of at least 60° from the cone axis, as indicated by the two parallel dotted lines in the lower view of FIG. 2D, permits partial adjustment of the direction of incoming air by rotation of the plug 35 within hole 34. One preferred orientation of plug 35 corresponds to an angle of 135° between the direction of the axis of tube 5 and the axis of hole 37, which imparts both lateral rotational and downward components to the motions of the inrushing sampled air.

The upper end of tube 5 has an upper collar 38 that fits snugly into an upper funnel-shaped portion 39 that can be locked onto an upper fan assembly or portion 41 by means of two lock slots 43, 43' and lock screws 45, 45' of FIG. 3B. A simple twisting motion of portions 39 and 41 relative to each other causes the two portions to get locked together or to get unlocked from each other. This simple locking and unlocking feature facilitates access to the inside of tube 5 for cleaning and rinsing purposes.

The funnel-shaped portion 39 yields at the outlet of sampling tube 5 an enlarged cross section which slows down the air velocity and thereby reduces the entrainment of water droplets by the exiting air stream. To further reduce the entrainment, funnel-shaped portion 39 may also include an inserted screen or gauze made of hydrophobic material having numerous perforations or an otherwise highly open structure that will not interfere with the air flow, while serving to retain most water droplets. The minimization of entrainment is especially important when the PHTLAAS is to operate at a high sampling rate or in a nearly horizontal orientation.

Figure 13:
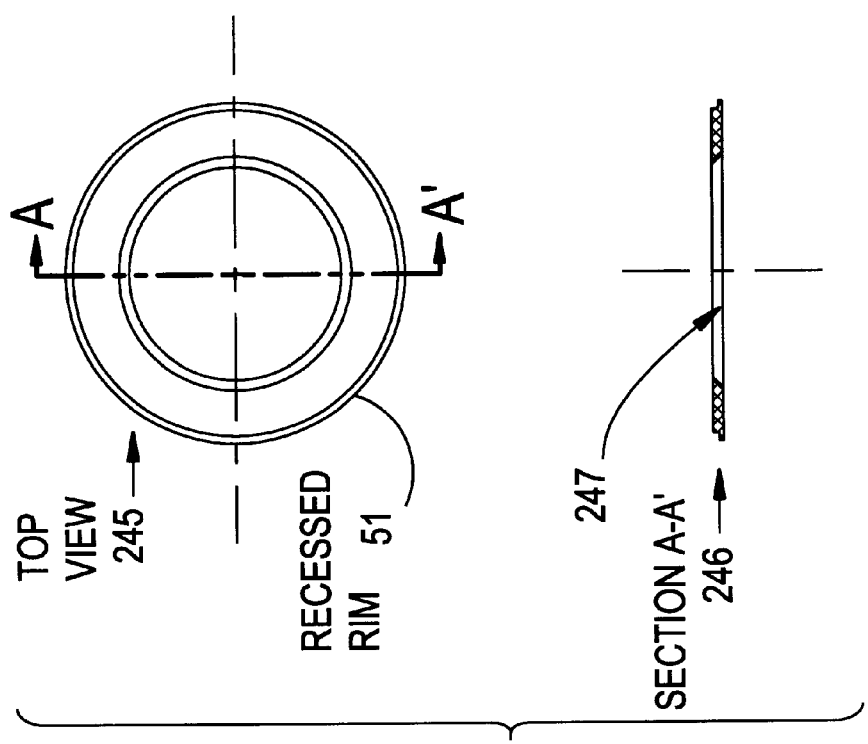
FIG. 13 is a top view and a corresponding axial cross-sectional view of the fan base plate or baffle 47 of FIG. 5.
Figure 9:
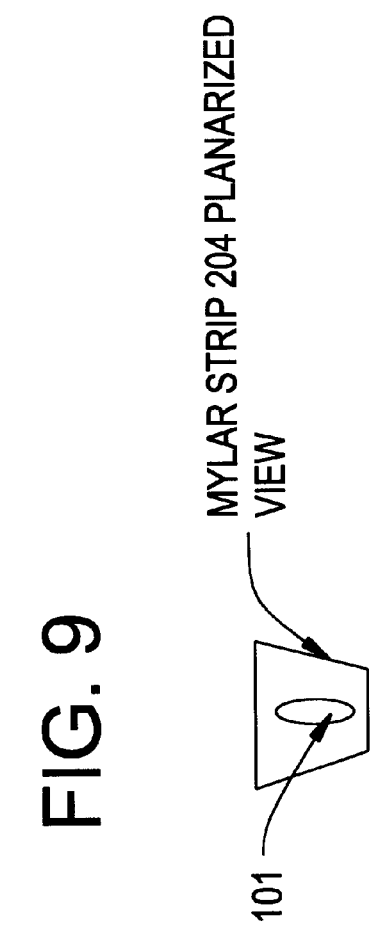
FIG. 9 is a planarized view of the flow control slit 104 of FIG. 5.

Between portions 39 and 41 is a disk-shaped baffle 47 [FIG. 2A] with a central hole 247 [see FIG. 13] through which air is drawn axially from the interior of tube 5 when the fan rotor 7 is operating. The air is discharged radially outward between blades 48 of the rotor. Baffle 47 also serves as the base of the fan. The air suction is most efficient when the lowest portion of blades 48 is within about 1 mm of baffle 47. To maintain the required spacing, a spacing grid 49 is inserted between the recessed rim 51 of baffle 47 [see FIGS. 5 and 13] and the slotted surface 53 of the fan assembly 41 [FIG. 3B].

The fan assembly 41 comprises a centrifugal fan 7 affixed to a shaft 55 that is rotated by motor 9 [FIG. 3B]. Electrical leads 57 [FIG. 1] supply direct current to motor 9 from a battery or DC power supply [not shown]. Motor 9 is fitted into a motor holder 58 and kept in place by screws 59, 59' [FIG. 2A]. Around motor holder 58 may be disposed an annular liquid reservoir 11 [FIGS. 2B and 3A]. A tubule 15 feeds liquid absorbent from reservoir 11 or 161 to liquid inlets 13, 13'. The suction of the fan is sufficient to draw liquid from reservoir 11 or 161 into tube 5 at the preferred rate of about 1 mL/minute, and a small needle valve 77 [FIG. 4] permits fine adjustments of the liquid flow rate. Reservoir 11 may include a port 61 for introduction of the liquid and a porous Teflon cap 63 which permits air to breathe into the reservoir without allowing the liquid to leak out.

As shown in FIG. 4, reservoir 11 comprises an annular chamber 65 between two concentric cylindrical walls 67 and 69 extending from an annular disk 71, and a top plate 73. A needle valve 77 controls the liquid flow between chamber 65 and a channel 79 that leads to tubule 15 and liquid inlets 13, 13'. Channel 79, grooved within disk 71, is confined by a bottom plate 75.

Tube 5 is most conveniently made of plastic material, such as polyacrylate or polycarbonate, which, however, is not readily wetted by aqueous solutions. For good wetting, tube 5 should be preferably lined with a hydrophilic polymeric coating or made of glass, quartz or Vycor, but the latter materials may be too fragile if left unprotected. To overcome the problem of excessive fragility, an alternative embodiment of the invention, ruggedized for field use, is shown in FIG. 5. Here the reservoir 11 and needle valve 77 of FIGS. 2–4 are dispensed with altogether. In lieu of these components, a drain valve 100 is embedded in the drain portion 117. As shown in FIG. 7, valve 100 comprises a Teflon [polytetrafluoroethylene] stem 205 with a slightly larger middle portion 207 which fits tightly into hole 120 of drain body 111 and through which is drilled a drain opening 206. A knob 203 with a roll pin 202 permit easy rotation of valve 100 to an open or closed setting. A groove 201 holds a fine retaining O-ring [not shown] that assures secure seating of valve 100 within hole 120 in the body 111 of drain portion 117 [FIGS. 5 and 6].

Body 111 is a cylindrical block made preferably of a plastic material, such as polyacrylate or polypropylene, in which is cut a funnel-shaped inverted conical cavity 27 at whose apex is drilled a drain port 29 through which drainage of liquid is controlled by valve 100. Around the outlet of port 29 is an annular cavity 30 into which is glued or tightly fitted a threaded cap 31 in which had been cut a central hole which clears the inner wall 32 of the annular cavity. Above the conical cavity 27 is a cylindrical cavity 116 into which can be fitted the outer tube 106 of FIGS. 5 and 8. Equally spaced threaded holes 118 are made in the wall of cavity 116 for three set screws [not shown] that are provided to permit firm attachment [or separation] of drain portion 117 to [or from] tube 106.

Valve 100 is normally closed, so that the liquid absorbent within the sampler tends to collect in the conical cavity 27 of drain portion 117 above valve 100. In this embodiment, a predetermined volume, preferably 5–20 mL, of liquid absorbent is injected into the PHTLAAS through slit 104 and air inlet 102 before the start of a sampling operation. This liquid collects at first within conical cavity 27. As soon as fan rotor 7 is turned on, part of the downward in-rushing air impinges on the collected liquid and causes a part of the liquid to spread as a moving film over the interior surface 103 of an inner glass tube 105, which constitutes the primary air sampling tube of the PHTLAAS, and also over the unobstructed lower interior surface 127 [FIG. 8] of a protective outer tube 106. Protective tube 106 may be of plastic material, preferably Lexan [polycarbonate]. Tube 106 serves to (a) connect the drain portion 117 to an upper funnel portion 239 through a coupling ring 139 and (b) provide an air inlet 102 through which the sampled air is drawn into the PHTLAAS. Over inlet 102 is flow control slit 104 [FIG. 5], which is a straight elongated opening 101 with rounded (semicircular) shorter edges cut out of a strip 204 [FIG. 9] of metal or plastic, such as 0.1–0.2 mm thick Mylar, that is taped over inlet 102.

As shown in FIG. 8, the air inlet hole 102 is cut tangentially to the wall of tube 106, so as to yield a slight asymmetry in the configuration of inlet 102 and of the overlapping slit 104 [FIGS. 5 and 9]. This asymmetry is on the side that matches the rotation of the fan so that together with the centrifugal action of rotor 7 it serves to impart a tangential component, and hence turbulence, to the motion of the inrushing air. This assures that the entering air follows a swirling path, which results in swirling of the extractant, full wetting of the inner walls of the preconcentrator, and efficient analyte transfer from the air to the extractant.

The inner tube 105 [FIGS. 5 and 12] is made preferably of a wettable material such as glass or quartz. The term "wettable" as used herein, describes a material, on the surface of which a liquid will form a continuous liquid film, rather than discrete droplets or beads. For example, most plastics are not wettable by aqueous solutions because these liquids tend to bead up on the surface thereof. Clean glass or quartz, however, can be wetted by such liquids. Glass tube 105 is provided with a substantially flat flange 115 with a groove 125 for O-ring 152. To prevent cracking or shattering of the glass under harsh environmental conditions, such as vibrations, mechanical impacts or temperature extremes, tube 105 is secured and cushioned, as shown in FIG. 12, by three O-rings 151, 152, and 153, which are the only solid bodies that come in direct contact with the glass. O-ring 151, within groove 145, and O-ring 153, slipped over the outside of tube 105 right under flange 115, separate tube 105 from the coupling ring 139 which is connected to the protective outer tube 106 by set-screws [not shown] within three threaded holes 142 [FIG. 10]. O-ring 152 separates tube 105 from the funnel portion 239 that is clamped to ring 139 by three bolts [not shown] within holes 144 [FIGS. 10 and 12] and 243 [FIGS. 11 and 12]. The clamping of portion 239 to ring 139 results in a firm squeezing and seating of flange 115 by O-rings 152 and 153, while O-ring 151 renders tube 105 co-axial with ring 139 and outer tube 106. An air gap 126 separates the exterior of tube 105 from the interior of tube 106. There is also a fine air gap between an annular protrusion 237 from the lower base 236 of funnel portion 239, 1; which serves to prevent entry of fluids in the space between flange 115 and base 236, and the upper surface 128 of the flange.

In operation, the air to be sampled is drawn first into the lower part 107 of the outer tube 106 through the air inlet 102 and then upwardly through inner tube 105, upper funnel 39, and opening 247 in the fan base plate 47 into the centrifugal fan assembly 41. The fact that the air stream enters and leaves the inner tube 5 in directions substantially normal to the longitudinal axis thereof, together with the relatively high velocity of the air flow, contributes to a turbulent flow of the air through tube 105.

Figure 14:
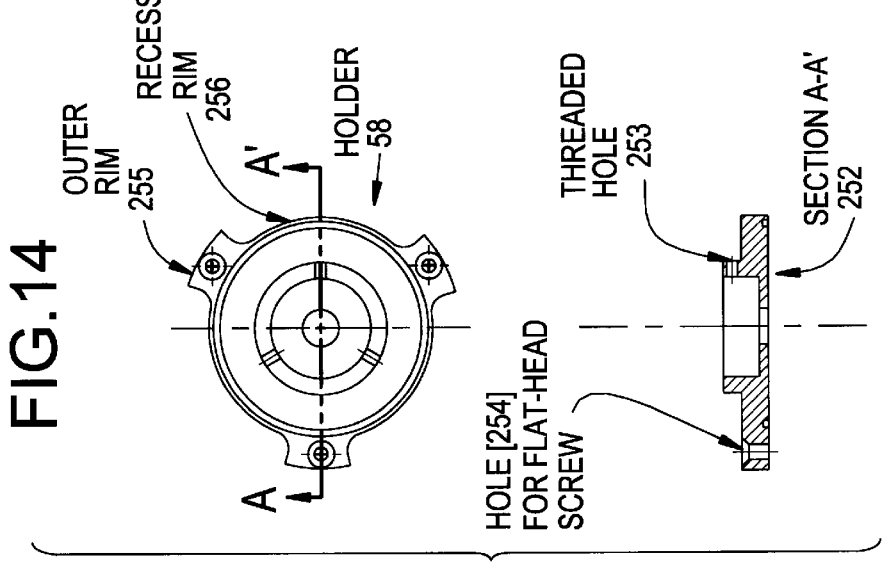
FIG. 14 is a top view and a corresponding axial cross-sectional view of the motor holder 57 of FIG. 5.

Referring to FIG. 5 and the Figures that are bracketed below, the air that is drawn through opening 247 of baffle 47 is impacted by rotor blades 48 of fan rotor 7 [FIG. 16D] and expelled through grid 49 [FIG. 16C] toward the wall 157 of cap 150 [FIG. 16A] and upwards between wall 157 and the recessed rims 256 of the motor and fan holder 57 [FIG. 14] and around motor 9, so as to finally exit through exhaust opening 159 [FIG. 16A]. As the air passes around motor 9, it removes the heat that is generated by the motor, thereby stabilizing the motor temperature and operation.

The open and mostly unobstructed flow path from air control slit 104 through tube 105, upper funnel 239, opening 247, fan rotor 7, grid 49, and cap 150 results in a total pressure drop through the operating PHTLAAS of only about 2 inches of water, which permits the use of a light-weight and relatively low-power-consuming centrifugal fan, which, in turn, leads to the compact and portable overall configuration of FIG. 5.

The transitions in flow cross-section, first between those of the air entrance slit 104 and outer tube 106 and next between tubes 106 and 105, also contribute to an increased entrapment of aerosol particles in the liquid film which covers the insides of tube 105 and of the lower part of tube 106, which in turn yields a further improvement in their collection efficiency.

The collection of the analyte-enriched sorbing liquid can be effected as follows. To collect a single liquid sample over a selected time interval, e.g., 5–10 minutes, valve 100 is kept closed, so that the liquid sorbent accumulates in the cavity 27 and evaporates partly therein, thereby yielding a preconcentrated sample of analyte in a small volume of liquid, e.g., 1–4 mL. At the end of the sampling period, valve 100 is opened and the preconcentrated liquid is allowed to drain from cavity 27 into collection vial 19. To collect multiple consecutive liquid samples for continuous near real-time monitoring of the compositions of the sampled air, the time intervals between successive samplings can be adjusted, e.g. to between 6 seconds and 10 minutes, with separate liquid samples being introduced into a multiplicity of separate vials, each of which can be properly tagged and correlated with the sampling time interval.

To improve wetting of the interior wall 103 of tube 105, an ionizable or otherwise long-chain hydrocarbon detergent solution is included in the extractant, such as sodiumdodecyl sulfate, or cetyl-trimethyl ammonium bromide. Preferably, surfactants of the Triton series, manufactured by Rohm and Haas Company, having the general formula $(CH_3)CCH_2C(CH_3)_2—C_6H_4—(OCH_2CH_2)_nOH$, where the alkane chains are attached to a benzene ring in the para position and the average value of n is 9.5 for Triton X-100, or 7.5 for Triton X-114, as discussed in *Environmental Science and Technology*, Vol.23, No. 7 (1989), page 833, are used as the wetting agent in a concentration of about 0.1 gram per liter of water. This wetting agent permits the use of a small volume of extractant, e.g., 5 mL, while still maintaining acceptable wetting of the interior wall 103 of tube 105.

To maximize preconcentration of the analyte, it is desirable to minimize the volume of sorbing liquid collected in vial 19. This minimization can be achieved by allowing the sorbing liquid to collect in the conical cavity 27 for a desired period of time, for example 6–10 minutes. While the liquid collects, it partially evaporates and thereby reduces the volume subsequently collected by drainage into vial 19.

In some applications, it may be desired to have the liquid sample analyzed by an instrument that does not readily accept aqueous solutions, e.g., a gas chromatograph, an ion mobility spectrometer or a mass spectrometer. In such cases, the extractant may also comprise a small volume fraction [e.g., 1–5%] of a relatively nonvolatile water-soluble organic compound, such as ethylene glycol [boiling at 198° C.] or glycerol [boiling at >290° C.], that preferentially absorb an organic analyte of interest. After running the sampler for a sufficient time for water to evaporate from the initially injected liquid, the residual nonvolatile organic compound can be rinsed down with a volatile organic liquid of low viscosity, such as methanol or ether, and collected in vial 19 for subsequent analysis.

In a constructional model of the PHTLAAS of FIG. 5, tube 105 has a length of about 18 cm and an inner diameter of about 2.7 cm. Air is drawn through the sampler at a rate of about 0.2–0.3 cubic meters per minute, in a swirling, highly turbulent motion, which assures rapid transfer of trace analytes to the liquid film which covers the interior surface 103 of tube 105. The maximum dimensions of this PHTLAAS are 10 cm diameter and about 50 cm total length. Its total weight, excluding the power pack, is about 700 g. The weight of the power pack depends on the choice of batteries and their replacement frequency. The required power is <20 watts.

To operate the PHTLAAS of FIG. 5, a small volume of liquid extractant, e.g., 8 mL, is injected into tube 106 through slit 104. Fan rotor 7 is then actuated so as to draw air via inlet 102 through the PHTLAAS at a rate of about 250 L/min. The partly downward, highly turbulent and swirling motion of the in-rushing air, impinging upon the injected liquid extractant, causes the latter to wet the inner wall 103 of tube 105 and to collect from the air a substantial fraction (usually 20–40%) of air contaminants, including vapors and aerosols in the respirable size range of about 1–10 microns. After sampling the air for a measured length of time, e.g., for 3–6 minutes, fan rotor 7 is turned off, and the liquid extractant is allowed to drain through valve 100 into collecting vial 19, from which it can be transferred to an analyzer or an indicator tape (not shown).

Although the PHTLAAS is normally operated in a vertical orientation to facilitate drainage of analyte-enriched liquid, it can also be used to sample adsorbable vapors or aerosols in an inclined or even horizontal orientation, provided that the sampling is followed by one or more rinsing steps in which a sufficient volume [e.g., 5–10 mL] of rinsing liquid is injected into the sampler as it is being operated in the vertical orientation for a brief time interval [e.g., ~1 minute], after which the rinsing liquid is allowed to drain into vial 19.

When it is desired to sample air continuously for an extended time, e.g., for several hours rather than several minutes, then it is necessary to provide an auxilliary liquid reservoir and pump [not shown] to feed liquid absorbent into the PHTLAAS at a rate that is sufficient to compensate for evaporation [usually ≦1 mL/minute]. The liquid may be fed through inlets 240 of FIG. 11 or through a liquid inlet 303 to the air intake adapter 301 of FIG. 17. In that mode of use, it may also be desired to drain the analyte-enriched liquid continuously, rather than intermittently, through port 29. To facilitate such continuous drainage, a fine air suction tubule [Line A of FIG. 18] preferably made of thin hydrophobic material, such as polytetrafluoroethylene, may be inserted through opening 206 of opened drain valve 100 or through the three-line solenoid valve of FIG. 18. This air suction tubule should be long enough to provide a connecting channel between the inside of vial 19 [FIG. 5 or 18] and the top of the upper conical cavity 249 [FIG. 11], so as to effectuate a sufficient suction within vial 19 to permit easy drainage of liquid thereto through port 29 or through Line B of FIG. 18.

Figure 19:
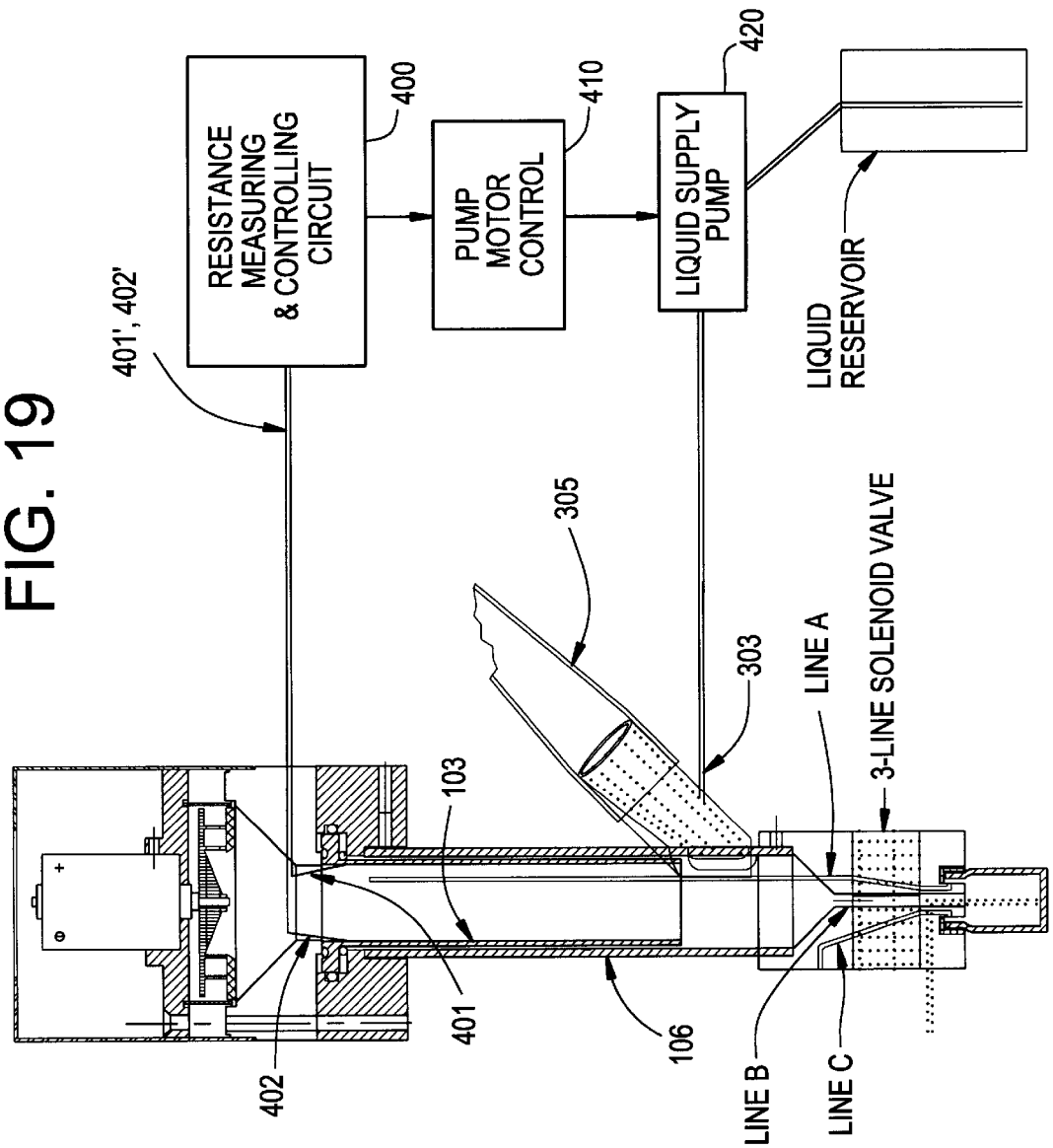
FIG. 19 is a schematic block diagram of a means of controlling the liquid input into a continuously operating PHTLAAS.

Several alternative or complementary modes of operating the PHTLAAS are best explained with reference to FIGS. 17–19. FIG. 17 depicts an arrangement where the PHTLAAS is separated from the sampled air by an enclosure 300, which comprises a top surface 306 and a lateral rim 304. Such an enclosure may appertain to a moving vehicle or to a stationary instrument case. To draw air from above the top 306 of enclosure 300 to the sampler's air inlet 102, a flexible tubing 305 is connected to nipple 302, which forms part of top 306, to an air intake adapter 301, which leads to the air intake 102. Adapter 301 is a hollow transition piece of smoothly varying internal cross section, such that its upper end matches the relatively large inner diameter [I. D.] of tubing 305, whereas the lower end matches the shape and size of either the flow control slit 104 of FIG. 5 or of an alternative circular or elliptical opening [not shown] having a smaller diameter than the I. D. of tubing 305. For instance, the I. D. of tubing 305 may be 1" or larger, whereas that of the inlet opening 102 may not exceed 0.75". In any case, the airflow line leading from opening 308 through tubing 305, intake adapter 301, and air inlet 102 should be free of obstructions and as smooth as practicable to minimize friction and discontinuities at which particles might tend to pile up.

It may be noted that in FIG. 17, the sampled air is first drawn downward from the top through nipple 302 into tubing 305 and thence through adapter 301 into air inlet 102, whence it is drawn upward towards the centrifugal fan. The reversal in flow direction at the air inlet has a similar effect to that of an impactor in forcing aerosol particles to impinge against the wetted walls of the sampler, which should contribute to a further improvement in the efficiency of collection of aerosol particles.

For continuous sampling over several hours or days, the sorbing liquid may be continually supplied to the PHTLAAS by a metering pump 420 [FIG. 19] through a liquid inlet tubule 303 which pierces the wall of intake adapter 301 or of tubing 305. To keep withdrawing analyte-enriched samples from the PHTLAAS for testing by an appropriate sensing device, which may comprise one or several complementary sensors, a PHTLAAS-sensor interface may be provided, such as that shown in the schematic diagram of FIG. 18, wherein the drain portion 117 of FIG. 5 has been modified so that a three-line solenoid valve is substituted for the manual valve 100. Line A of the three-line valve serves to connect vial 19 to the low-pressure section of the PHTLAAS so as to effectuate a slight vacuum in vial 19 to facilitate drainage of liquid from the conical cavity 27 into vial 19 when Line B is open. To draw liquid from vial 19 to a sensing device [not shown], Lines A and B are closed and a liquid sampling pump [not shown] is actuated. To facilitate withdrawal of liquid from vial 19 through a connecting line 322, Line C is opened, which allows outside air to enter vial 19 and thereby equalize the pressure in vial 19 with that of ambient air. This constitutes Step 1 of a programmable two-step cycle. Step 2 consists of closing Line C, opening Lines A and B, and shutting off the liquid sampling pump. This cycle can be caused to repeat automatically at predetermined times and/or time intervals by a programmable control circuit 330.

Another requirement for automated or semi-automated continuous operation of the PHTLAAS is the proper balance between the rate of replenishment of the sorbing liquid and the rate of its depletion by evaporation, entrainment or sample withdrawals. If the replenishment is excessive, too much liquid will accumulate within the sampler, which will result in partial flooding, increased liquid entrainment losses, and hence reduced collection efficiency. If the rate of replenishment is insufficient, the sampler may dry up, at least in part, which will also result in reduced collection efficiency. Therefore, the liquid input control system of FIG. 19 is provided for maintaining a near-optimal volume of liquid within the sampler.

FIG. 19 is a block diagram of a resistance-measuring and controlling circuit 400 connected by insulated leads 401' and 402' to two separate wires or strips 401 and 402, made of a non-corrodible material, such as gold or platinum, whose ends are disposed in the upper portion of the interior surface 103 of sampling tube 105. As long as that portion remains fully wetted, the resistance between wires or strips 401 and 402 along surface 103 will have a readily measurable value thanks to the conductivity of water and of aqueous solutions ($\geqq 10^{-7}$ ohm$^{-1}$–cm$^{-1}$). When a dry patch develops on surface 103 between the wires or strips 401 and 402, there will be a distinct jump in the resistance that is measured by circuit 400, which will cause the motor control 410 of a liquid metering pump 420 to increase the liquid pumping rate until the measured resistance falls back to a readily measurable value, at which time circuit 400 causes control 401 to reduce the pumping rate. In this manner, the liquid input rate is continually adjusted so as to maintain nearly full wetting of the surface 103.

The ability of the PHTLAAS to collect both vapors and aerosols from the sampled air should be especially useful in applications where a significant fraction of the airborne analyte may be in form of vapor (e.g., organometallic compounds, such as methyl mercury or tetraethyl lead), solid particles or liquid droplets.

The extractant that is to be used in preferred embodiments of the invention will depend on the analyte of interest. To dissolve lead compounds, such as lead oxide (PbO), lead carbonate ($PbCO_3$), or lead nitrate ($Pb(NO_3)_2$), a solution of acetic acid or acetate may suffice. To solubilize metallic lead, an oxidant needs to be added to the extractant. The effect of pH and of acetic acid, acetate, and oxidant concentrations in water on the rate of solubilization of metallic lead at 20° C. is shown in FIGS. 4–6 of the co-pending application Ser. No. 931,572. At a pH of 5 or less, as little as 0.1 M of sodium acetate or acetic acid plus 1 weight-% $H_2O_2$ suffices to yield an etching rate of about 10 microns/min, which implies that particulates in the respirable size range of <5 microns will completely dissolve in such a solution within a fraction of a minute.

Indeed, when 1-mL portions of an extractant containing 0.3 M acetic acid plus 3% hydrogen peroxide were added to 1-mg samples of powdered lead carbonate (passed through a 325×325 mesh gauze that retained particles of sizes >40 microns), lead oxide, or lead nitrate, complete dissolution of the powders occurred within less than a minute. It therefore appears that a solution containing 0.1–1 M of acetic acid or acetate ions plus 1–10% of hydrogen peroxide is adequate for the solubilization of lead-containing particulates, provided that its acidity is kept at a pH of 5 or less. Furthermore, for use with the PHTLAAS, the preferred concentration range is 0.1–0.3 M of acetic acid plus acetate ions and 1–3% of hydrogen peroxide.

If it is desired to monitor solely the lead content of respirable particulates, a coarse filter or filter-tape may be interposed at the air intake 102 of FIG. 5, so as to exclude the nonrespirable particulates from the collected samples. Alternatively, a flow-deflecting large-particle impactor [not shown] may be interposed at the air intake so as to collect the larger particles outside the PHTLAAS, while allowing the smaller particles to flow unhindered through the intake with the sampled air.

The analytical means that is to be used with vial 9 will again depend on the analyte of interest. For the detection of lead in aqueous solutions under field conditions, a colorimetric or electroanalytical method appears to be more cost effective than an alternative method based on atomic absorption spectroscopy (NIOSH Method 7082).

A simple and rapid colorimetric method for estimating lead concentrations in aqueous solutions consists of placing a droplet of the test solution on a lead indicator tape or strip, such as the commercially available "EM Quant Lead Test" strips from EM Science (Gibbstown, N.J. 08027, Catalog No. 10077-1) that are distributed by Alfa/Johnson Matthey (Ward Hill, Mass. 01835, Catalog No. 34933). These strips can be used directly with the extractant, without any intermediate steps. By comparing the color of the wetted strip with a color-comparison chart, one obtains an estimate of lead concentrations in the range of 15–500 ppmw (parts per million by weight). There is no interference from either the acetic acid or the hydrogen peroxide in the extractant.

A far more sensitive and more accurate quantitative detection method for dissolved lead in an aqueous electrolyte is anodic stripping voltammetry (ASV), as described, for instance, by DeAngelis et al. in *Anal. Chem.,* 48(14) :2262–2263 (1976) and 49(12):1792–1797 (1977). The supporting electrolyte was 1 M potassium acetate adjusted to pH 4.0 with acetic acid, which is fully compatible with the afore-disclosed liquid extractant. A portable instrument based on the work of Gunasingham et al., *J Electroanalytical Chemistry,* 186:51 (1985), may permit rapid and fairly accurate measurements of lead concentrations in switchable ranges of 50–700 ppbw (parts per billion by weight) and 500–3,000 ppbw.

An alternative electro-analytical detection method could be based on a lead-sensitive ion-selective electrode (ISE) whose lower detection limit for lead ions in acetate buffer was found by Heine et al., *Anal Chim. Acta,* 100:193–205 (1978), to vary between $10^{-8}$ M and $3\times10^{-7}$ M (corresponding to 2–60 ppbw). Such a method would be most attractive for field use if the ISE can be rendered insensitive to commonly encountered interferences.

The measurement time by either of the afore-mentioned colorimetric or electroanalytical methods is usually of the of the order of 1 minute.

To evaluate the applicability of alternative detection methods, it is helpful to consider a few numerical examples. Thus, a PHTLAAS sampling air containing $5\times10^{-5}$ g Pb/m$^3$ at a rate of about 300 L/min for 1 minute at a collection efficiency of 20% will yield $$0.20\times5\times10^{-5}\ (\text{g Pb/m}^3)\times300\ (\text{L/min})\times1\ \text{min}/1{,}000\ (\text{L/m}^3)=3\times10^{-6}\ \text{g Pb},$$

which, upon dissolution in about 5 mL of liquid extractant, yields a lead concentration of 600 ppbw. This concentration is readily measurable by ASV. Alternatively, if the concentration of airborne lead is in excess of $3\times10^{-4}$ g/m$^3$ and the sampling time is increased to 5 min or the liquid volume reduced to 1 mL, the EM Quant test strips could be used for a quick estimation of the air-borne lead concentration.

The selection of an appropriate analyzer for lead in aqueous solutions, whether colorimetric or electroanalytical, will depend on specific application needs. For instance, a satisfactory lead-sensitive ISE would be especially advantageous for field use because of its simplicity, low cost, and portability. However, any Pb-responsive ISE must be rendered compatible with the selected liquid extractant, insensitive to expected interferences (e.g., copper or calcium ions), and yet sensitive to about $10^{-6}$ g Pb/mL. The accuracy and reliability of any selected candidate ISE must be tested for various concentrations of lead and of likely interferences.

In another embodiment of the invention, the PHTLAAS can be used as a portable high-volume tritium sampler (HVTS). In one preferred procedure, a fixed volume $V_o$ of the aqueous absorbent is initially introduced into the sampler. When the blower is turned on, the swirling air causes a liquid film to wet the inner walls of the sampler tube, and the highly turbulent air flow results in good interchange of water molecules across the air-liquid interfaces within the tube. As shown in the parent application Ser. No. 08/255,712 and in a publication by Zaromb et al. in *Health Phys.* 72(3):480–484, March 1997, entitled "A novel portable grab sampler for tritiated water vapor," both of which are included herein by reference, this interchange results in the following relation between the concentration $c_v$ of tritiated water per unit volume of sampled air and the concentration c of tritiated water in the sampler when the volume of water remaining in the sampler has been reduced to about 10% of the initially injected volume:

$$c_v/c \simeq 288p'_{we}/T\ \text{g/m}^3\ (p'_{we}\ \text{in mm Hg}),$$

where $p'_{we}$ is the equilibrium vapor pressure of water at the absolute temperature T [in degrees Kelvin].

According to this relation, the ratio $c_v/c$ is independent, in first approximation, of the humidity of the sampled air. Thus, the tritium concentration $c_v$ in the sampled air is approximately proportional to the tritium level that is measured in the collected liquid sample, which is readily measurable by scintillation counting.

Another potential application of the PHTLAAS is in sampling for biological aerosols, especially those of fragile bacteria, such as *Escherichia coli.* When it is desired to detect such micro-organisms and measure their concentrations in air by bioassay methods, such as colony counts of live bacteria, the PHTLAAS offers an important advantage in that the relatively low pressure drop through the sampler also implies comparatively low velocities of the bacteria that are impacting its liquid film, which implies lower stress and higher survivability of fragile organisms.

To maximize the viability of fragile microorganisms, the absorbing liquid may be an aqueous solution of about 0.01–0.05% of a surfactant, such as Triton X-100 or Tween 80, plus 0.8% NaCl. To minimize changes in the salt concentration as water evaporates during sampling, one can (a) start with an approximately 20% lower concentration, i.e., about 0.6% saline, and (b) limit the total evaporation losses to not more than 40% of the initial volume, so that the final salt concentration will be not more than 20% above the optimum value of 0.8%. For instance, an initial volume of 8 mL of a 0.6% saline solution sampled for 5 minutes will yield a 0.96% salt concentration in a final volume of 5 mL for an evaporation loss rate of 0.6 mL/minute.

A better way of assuring an optimal liquid composition in the PHTLAAS is based on the operation of a PHTLAAS in a continuous mode rather than the just outlined intermittent mode. In continuous operation, both the amount of liquid in the sampler and the liquid composition can be maintained in a steady state by continually adding sufficient liquid to make up for the evaporation and entrainment losses. In the ideal case, where there is no entrainment, the liquid composition can be kept constant by adding pure water, since the initially introduced salt will not evaporate. If the sampling rate is raised to a point where entrainment losses are comparable to the evaporation losses, then one can maintain a 0.8% saline composition by using a make-up composition of 0.4% saline. Thus, by adjusting the make-up composition according to the ratio of entrainment losses to evaporation losses, one can, in principle, maintain the optimal composition of 0.8% Saline for any desired sampling time.

Of course, more hardy organisms, such as spores of *Bacillus subtilis* var. *niger* [BG], can readily survive in salt-free liquids.

EXAMPLE 1

In initial experiments with aerosols of BG spore agglomerates of 4 $\mu$m geometric-mean aerodynamic-mass diameter [with a geometric standard deviation of 1.735] dispersed in a wind tunnel, a PHTLAAS whose liquid sorbent contained substantially pure water plus 0.05% Triton X-100 was tested at an air sampling rate of 230 L/min. Its collection efficiency, as measured by the standard bacteriological assay for BG, was found to be 85(+10,−14)%.

From the foregoing, it can be seen that, by coupling a PHTLAAS with an appropriate detection means or method, there has been provided a simple, fast-acting and inexpensive analytical system for pre-concentrating and detecting trace levels of analytes, such as hazardous materials, and which is uniquely adapted for use in portable devices for rapid on-site detection and quantification of such analytes. The system is adaptable for use with multiple detection techniques, including photometric and electrochemical [e.g., amperometric] techniques, while providing greater sensitivity, wider measurable concentration range and greater flexibility than prior devices using such techniques.

Of special interest may be the monitoring of sampled air for biological agents or potential carcinogens by testing the collected sorbing liquid for biological matter or mutagenicity. In conjunction with various analyzers, the PHTLAAS can serve to monitor a variety of hazardous or illicit airborne substances, such as lead-containing particulates, tritiated water vapor, biological aerosols, or traces of concealed drugs or explosives. To check for exposure to potential carcinogens, the analyte-enriched liquid collected in vial 19 can be subjected to Ames tests or to alternative accelerated mutagenicity tests.

There will now be obvious many variations and modifications of the afore-disclosed embodiments to persons skilled in the art. Although the illustrative examples are addressed primarily to the monitoring of lead, tritium or bacterial spores, it will be obvious that similar approaches can apply to the monitoring of other hazardous substances, e.g., comprising cadmium, zinc, chromium, uranium, or compounds of these metals, miscellaneous carcinogens, and other toxic contaminants, that can be either absorbed directly in a suitable liquid extractant or solubilized therein from collected airborne particulates. All of these variations and modifications will remain within the scope of this invention if defined by the following claims.

I claim:

1. In apparatus for sampling an analyte from a gaseous medium, said analyte being in form of vapor or of liquid droplets or solid particulates, comprising a means for sampling a volume of said medium and collecting said analyte therefrom;

a tube having a gas outlet end and a liquid drainage end; and means for wetting an inner part of the tube with an analyte-sorbing or -suspending liquid;

the improvement comprising means for flowing the gaseous medium through an inlet opening and said liquid drainage end into the tube toward skid outlet end, over the liquid that is wetting said tube in direct contact therewith for trapping and preconcentrating the analyte in the sorbing or suspending liquid, and collecting from said drainage end an enriched liquid containing the preconcentrated analyte;

wherein said liquid drainage end is directed towards a container means for holding draining or injected liquid; and wherein said inlet opening is so configured as to impart to the gaseous medium within said sampling means near said inlet a flow direction at a substantially acute angle that is that is at least partly opposite to that of the flow of the gaseous medium through said tube;

said opening thus also forming part of said wetting means by causing at least partial impingement of said gaseous medium against the liquid that is held within said container means.

2. The improvement of claim 1, wherein said inlet opening is directed partly downward when the flow through said tube is upward.

3. The improvement of claim 2, wherein said inlet opening is asymmetric so as to also impart a rotational component to the motion of the sampled gaseous medium.

4. The improvement of claim 3, wherein said asymmetric inlet opening is matched with an air intake adapter which facilitates sampling of air that is separated from the sampler by an enclosure.

5. The improvement of claim 1, comprising a fan that is located near said outlet end and a funnel-shaped cavity means between said outlet end and said fan that reduces entrainment of liquid by the gaseous medium and thereby facilitates operation of the sampling means in an inclined orientation that world otherwise cause excessive entrainment.

6. The improvement of claim 5, comprising a drain means for draining said analyte-containing liquid into a container means.

7. The improvement of claim 1, wherein said inlet opening is a beveled hole fitted with a plug that is in the shape of a truncated cone and that has a straight hole drilled therethrough at an angle from the cone axis that permits partial adjustment of the direction of the incoming gaseous medium by rotation of the plug within the beveled hole.

8. The improvement of claim 6, wherein said tube is an inner tube that is enclosed within a larger outer tube and said inlet is formed within said outer tube, so that the flow of said gaseous medium must get partly constricted as it passes from said larger outer tube into said inner tube.

9. The improvement of claim 6, wherein the interior of said tube is made of a readily wettable material, such as glass, quartz, or Vycor.

10. The improvement of claim 3, comprising a means for removing large non-respirable particles from the gaseous medium that is entering said inlet opening.

11. The improvement of claim 10, wherein said removing means comprises a coarse filter or filter-tape interposed at the inlet opening.

12. The improvement of claim 10, wherein said removing means comprises a flow-deflecting large-particle impactor interposed at the inlet opening so as to collect the larger particles outside the sampler, while allowing the smaller particles to flow unhindered through the inlet with the gaseous medium.

13. The improvement of claim 1, comprising a reservoir means and a liquid supply means for continuously feeding said liquid into said tube.

14. The improvement of claim 4, wherein said air intake adapter or a tube connected thereto comprises an opening through which liquid can be introduced into said sampler.

15. The improvement of claim 13, wherein said liquid supply means comprises a control circuit which assures that the wetting of the interior surface of said tube is nearly complete.

16. The improvement of claim 15, wherein said control circuit comprises a circuit for measuring the resistance between two separated wires which may be in electrical contact with the liquid that may be wetting said tube.

17. The improvement of claim 1, wherein said supply means utilizes the suction of the fan to draw liquid from the reservoir means into said tube.

18. The improvement of claim 17, wherein said supply means comprises a needle valve for controlling the liquid flow rate.

19. The improvement of claim 13, comprising a handle for hand-carrying said sampling means and wherein said reservoir means forms part of said handle.

20. The improvement of claim 6, wherein said container means comprises a vial and an attachment means for readily attaching or detaching said vial to or from said drain means.

21. The improvement of claim 6, comprising transfer means for automatically transferring analyte-enriched liquid from said container means to a sensor means at programmable time intervals.

22. The improvement of claim 20, wherein said attachment means comprises threads that match threads in said vial so as to permit quick attachment or removal of the vial by a screwing or unscrewing action.

23. The improvement of claim 6, wherein said drain means comprises a tubule leading from said container means to said outlet end whereby the pressure within said container means is reduced sufficiently to permit continuous draining of analyte-enriched liquid into said container means.

24. The improvement of claim 5, comprising quick connect/disconnect means for connecting said fan to said funnel-shaped cavity means.

25. The improvement of claim 24, wherein said connect/disconnect means comprises lock slots and lock screws.

26. The improvement of claim 1, comprising means for detecting the pre-concentrated analyte within said analyte-enriched liquid.

27. The improvement of claim 26, wherein said detection means is photometric or electro-analytical.

28. The improvement of claim 27, wherein said detection means comprises an optical fiber.

29. The improvement of claim 27, wherein said photometric device is an analyte-indicating tape or strip.

30. The improvement of claim 27, wherein said electro-analytical device is an anodic stripping voltammetry instrument.

31. The improvement of claim 27, wherein said electro-analytical device is an analyte-responsive ion-selective electrode.

32. In a method for preconcentrating an analyte in a gaseous medium, said analyte being in form of vapor or of liquid droplets or solid particulates, comprising the steps of:

disposing a length of wettable material within a container;

wetting one part of the wettable material with an analyte-sorbing liquid so that the liquid moves toward one end of the wettable material;

flowing the gaseous medium through an inlet opening into the container, over the liquid that is wetting said material in direct contact therewith for trapping and preconcentrating traces of analyte in the sorbing liquid, and collecting from the one end of the wettable material the sorbing liquid containing the preconcentrated analyte;

the improvement comprising the steps of injecting an initial volume of said liquid into said container, causing the flowing gaseous medium to impinge upon said liquid within said container at a substantially acute angle so as to spread part of the liquid over a substantial surface area of said wettable material.

33. The improvement of claim 32, which comprises monitoring sampled air for potential carcinogens by testing the collected sorbing liquid for mutagenicity.

34. The improvement of claim 32, which comprises monitoring sampled air for radioactive substances, such as tritiated water, by testing the collected sorbing liquid for radioactivity.

35. The improvement of claim 32, which comprises monitoring a sampled aerosol for biological agents by testing the collected sorbing liquid for biological matter.

36. The improvement of claim 32, comprising the step of detecting or measuring the concentration of the analyte by a photometric or an electro-analytical method.

37. The improvement of claim 36, comprising the step of transferring the analyte-enriched liquid to an analyzer or an indicator tape.

38. The improvement of claim 36, comprising the step of monitoring the analyte-enriched liquid in situ with a built-in sensor.

39. The improvement of claim 36, wherein said photometric method utilizes a fiber-optic detector.

40. The improvement of claim 32, wherein said electro-analytical method utilizes a miniaturized amperometric sensor.

41. The improvement of claim 32, wherein said electro-analytical method utilizes an analyte-responsive ion-selective electrode.

42. The improvement of claim 32, wherein said liquid comprises mostly water and a small volume fraction of a relatively nonvolatile water-soluble organic compound, such as ethylene glycol or glycerol, that preferentially absorb an organic analyte of interest and comprising the steps of:

initially injecting a predetermined volume of said liquid;

causing the gaseous medium to flow for a sufficient time for water to evaporate from said initially injected liquid;

rinsing down the residual nonvolatile organic compound with a volatile organic liquid, such as methanol or ether; and collecting the rinsings for analysis.

43. The improvement of claim 32, wherein a near-optimal composition of said sorbing liquid is maintained by appropiate adjustments of the compositions of the initially injected liquid and of any subsequently added liquid.

44. In a method for monitoring the concentration of an airborne analyte, said analyte being in form of vapor or of liquid droplets or solid particulates, comprising the steps of introducing a volume of air into a liquid-absorption air sampler at a substantially acute angle to a wettable inner wall, the improvement comprising the steps of first operating the sampler in a substantially nonvertical orientation or with insufficient liquid, whereby said inner wall is insufficiently wetted, and thereafter rinsing down parts of any analyte that is retained at said inner wall by injecting a sufficient volume of liquid into said sampler and operating the sampler in a substantially vertical orientation for a sufficient time to effectuate proper wetting of said inner wall, and thereafter allowing said liquid to drain down the inner wall and be collected for analysis.

45. The improvement of claim 5, wherein entrainment is further reduced by a hydrophobic screen within said funnel-shaped cavity.

46. The improvement of claim 6, wherein the internal surface of said tube is lined with a hydrophilic polymer.

* * * * *